(12) United States Patent
Ganshorn

(10) Patent No.: US 6,461,312 B1
(45) Date of Patent: Oct. 8, 2002

(54) METHOD FOR CREATING AN INDIVIDUAL MOVEMENT AND LOAD PROFILE AND A PORTABLE ERGOSPIROMETER

(76) Inventor: Peter Ganshorn, Goldgrund 3, D-97702 Münnerstadt (DE)

( * ) Notice: Subject to any disclaimer, the term of this patent is extended or adjusted under 35 U.S.C. 154(b) by 0 days.

(21) Appl. No.: 09/668,224

(22) Filed: Sep. 22, 2000

(30) Foreign Application Priority Data

Oct. 29, 1999 (DE) .......................................... 199 52 164

(51) Int. Cl.[7] .............................................. A61B 5/103
(52) U.S. Cl. ........................ 600/587; 600/300; 600/595
(58) Field of Search ................................. 600/300, 595, 600/587; 128/897

(56) References Cited

U.S. PATENT DOCUMENTS

| | | | | |
|---|---|---|---|---|
| 5,628,310 A | * | 5/1997 | Rao et al. | 600/317 |
| 6,102,856 A | * | 8/2000 | Groff et al. | 600/301 |
| 6,241,684 B1 | * | 6/2001 | Amano et al. | 600/531 |

* cited by examiner

Primary Examiner—Robert L. Nasser
Assistant Examiner—Patricia Mallari
(74) Attorney, Agent, or Firm—Edwin D. Schindler

(57) ABSTRACT

The invention concerns a method for creating an individual movement and load profile, where the absolute altitude is measured continuously, the movement and/or acceleration is recorded in all three directions in space, and the physiological load upon the test subject is calculated from the path and altitude profile and the cardial and pulmonary measured variables.

3 Claims, 1 Drawing Sheet

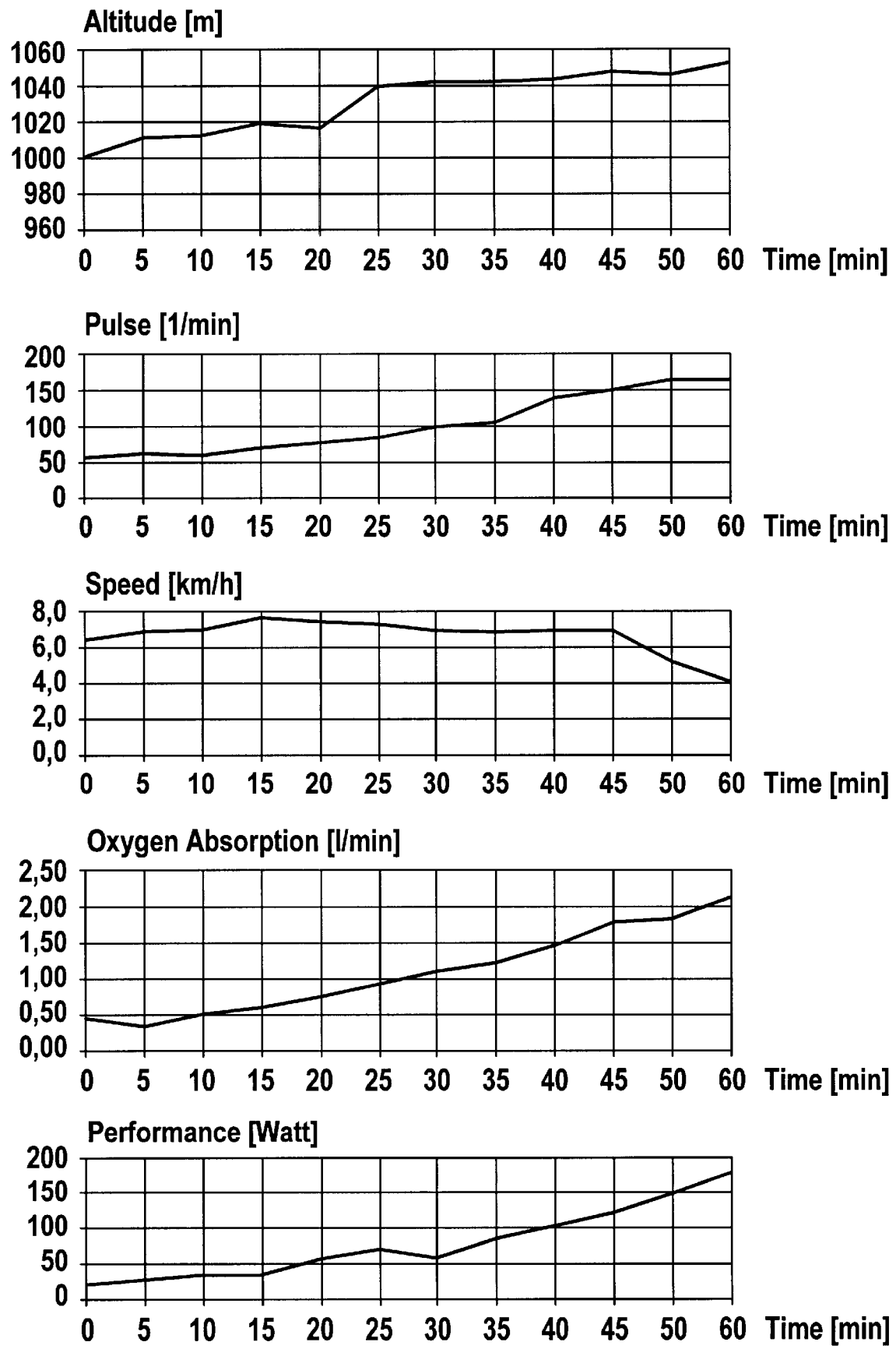

METHOD FOR CREATING AN INDIVIDUAL MOVEMENT AND LOAD PROFILE AND A PORTABLE ERGOSPIROMETER

BACKGROUND OF THE INVENTION

1. Technical Field of the Invention

The invention concerns a method for creating an individual movement and load profile using, for example, a portable ergospirometer for recording cardial and pulmonary measured variables for humans or animals and a portable ergospirometer.

2. Description of the Prior Art

Among other areas, movement and load profiles are necessary in occupational medicine, in training theory or for testing new materials for garments, e.g. for new footwear. Thereby, the movement of a test subject is usually recorded in the horizontal direction to record individual exertion or also to determine the scope of training. Effectively the load also depends on movement in the vertical direction as well as on the oxygen content of the ambient air, which changes with the absolute altitude.

Using ergospirometry, the tidal volume, the respiratory rate and the oxygen consumption of humans and animals can be measured under exertion. This allows the reaction of the cardiovascular system to exterior, generally defined, specific loads to be determined. Among other things, it is known to subject test persons on a bicycle ergometer to a certain physical exertion, for example, the test subject has to produce a continuous performance of 100 W. Using the ergospirometer, there is continuous measurement of the tidal volume, the composition of the expired air and various cardial parameters, such as the pulse. These allow the effective physiological loading of the test subject to be calculated, i.e. the effective biological performance the test subject must exert to produce 100 watts on the bicycle ergometer, whereby from experience a person has an efficiency ratio of approximately 30%, i.e. in the above mentioned example the person has to produce about 330 W. In a similar way, the test persons are subject to a defined load on a treadmill ergometer. Furthermore, portable ergospirometers are known, which are used especially for rehabilitation measures after cardiovascular diseases or in occupational or sports medicine, where the test subject carries a portable device, usually on his back, to record all cardial and pulmonary measured variables and where the physiological reaction to various loads, for example, different labour processes, can be recorded.

As concerns the methods known to date for creating egospirometric load profiles, it is to be considered disadvantageous that with stationary bicycle or treadmill ergometers respectively only a specific load can be exercised upon the test subject. To simulate realistic everyday situations and the physiological reactions of the test subject to such situations, these stationary devices are unsuitable. Although, portable ergospirometers can fulfil the task of a continuous measurement of the variables of interest under realistic conditions, for example, in the workplace or for a sports person during training, they are not able to record the effective, objective, external loads that a test person is subject to because they solely always only measure the physiological reaction of the test subject to such loads. As is known to a person skilled in the art, the reaction of the test subject, however, always depends on individual circumstances, i.e. when an objective, similar external load is applied, different test subjects show different physiological reactions.

SUMMARY OF THE INVENTION

Starting from the state-of-the-art, the invention has the object of providing a method for creating a movement and a load profile, and in a further development, an individual ergospirometric load profile, and a portable ergospirometer for executing the method. Thereby not only the physiological reactions of the test subject but also the effective physical loads can be measured, and the load can be recorded under the most varied environmental conditions and realistic everyday situations.

In accordance with the invention, this task is solved therein that the absolute altitude is continuously measured and the movement and/or acceleration is recorded in all three directions in space.

The central idea of the invention provides that to create a movement and a load profile, the movement and acceleration in all three directions must be recorded to receive complete information about the movement profile of the test subject. Thus it is possible that, for example, in occupational medicine, the movement sequences of the worker are recorded, or in training theory, the actual scope of the training of an athlete, as well as the durability of a new garment can be measured, if the absolute movement can be recorded, i.e. the actual distance a test subject has travelled using new footwear. Devices by means of which the acceleration and/or movement can be recorded, and which determine the absolute altitude, can be embodied in diverse ways, or as described further below.

Particularly advantageous is the method for creating an ergospirometric load profile by means of which not only the cardial and pulmonary measured variables of the test subject are recorded by a portable ergospirometer known per se, but also the movement of the test subject in space. To that end, the absolute altitude and the horizontal movement and acceleration are continuously recorded. Using these measured variables, a path and altitude profile can be created, which in conjunction with the cardial and pulmonary measured variables, yields the actual load upon the test subject. It is known to a person skilled in the art that, for example, going uphill at a certain speed represents a substantially greater physical exertion than walking on the level at the same speed. Likewise, the absolute altitude is an important influencing variable for the effective load, because the oxygen content of the air decreases as the altitude increases. The conversion of the measured values into a path and altitude profile and deriving the effective physical exertion of the test subject is possible for a person skilled in the art. For example, when going uphill additional lifting force must be used in contrast to walking on the level. Walking at different speeds, which can also be determined from the path profile, is expressed in the different reactions of the test subjects.

The advantage of the invention consists therein that with these methods not only the physiological reactions and the oxygen consumption of the test subject but also the effective movement through space is measured, which is of decisive importance for the magnitude of the actual load. Thus, realistic, measurement results are achieved which correspond to the natural conditions.

Portable ergospirometers to execute the method are the subject matter of the subclaims.

To execute the method a portable ergospirometer is necessary as known per se in the state of the art, i.e. cardial, pulmonary and motional physiological measured variables are recorded for humans or animals, and the ergospirometer has devices to record, store, evaluate or transmit such data.

The energy supply is usually provided by batteries. To execute the inventive method, furthermore, devices are provided by means of which the absolute altitude of the test subject or the ergospirometer can be determined, as well as sensors to record the movement and/or acceleration in all three directions in space. These devices and sensors can be implemented in diverse ways, as explained below. Thereby, it is irrelevant in accordance with the invention whether the measured values are processed directly in the ergospirometer itself or whether they are solely stored and read out later. The person skilled in the art can create a path and altitude profile from the measured values and determine the respective current speed of the test subject, i.e. map the actual movement of the test subject in space. Furthermore, it is possible for the person skilled in the art, using this profile and the usual measured values, to convert the actual physical load into the biological exertion of the test subject, especially when climbing and descending.

To record the absolute altitude, it is proposed to use a barometer. They are well known in the state of the art and continuous recording of the absolute altitude, adjusted by the weather-related changing air pressure, is possible without problems. An especially simple embodiment consists therein to use an electronic barometer, in particular a piezoelectric one. It enables the direct further processing of the electric measured signals.

To record movement in the horizontal direction, acceleration detectors or sensors on a mechanical or electronic basis can be are used, which are well known in the state of the art. Here, too, continuous recording of the measured variables and their further processing is possible in a simple way.

The three-dimensional movement through space can be recorded especially simply using a GPS device. Especially when a differential GPS device is used, deviations of less than 1 m from the actual position can be achieved and guarantee sufficient measuring accuracy when recording movement through space. If the GPS device has an electronic interface, it is possible to read out the data and process it to obtain a path profile in an especially simple way.

Furthermore, it is proposed to provide the ergospirometer with an infrared interface to transmit all measured variables, and the data determined therefrom, to a further evaluation or storage unit. Corresponding devices are known to the person skilled in the art. Thus, the portable ergospirometer can be used in mobile applications as well locally as a stationary unit.

BRIEF DESCRIPTION OF THE DRAWING FIGURE

Further details, features and advantages of the invention can be taken from the following description part in which with the aid of drawing the invention is explained in greater detail. It shows:

FIG. 1 the load profile of a test subject, in conjunction with a path profile.

DETAILED DESCRIPTION OF THE DRAWING AND PREFERRED EMBODIMENTS

The diagrams shown in FIG. 1 record different measured values. The first line records the respective absolute altitude of the test subject during the load measurement. It is decisive for both the oxygen content of the air as well as that greater performance is required when going uphill than on the level. The second line records the pulse of the test subject, which provides information especially about the biological exertion and the physiological reaction to exterior loads. The third line presents the speed at which the test subject moves in the horizontal direction. It is also important for the actual physical load because movement at higher speed requires a greater power output. Line 4 shows the oxygen quantity consumed by the test subject. It is determined with the aid of the measurement of the tidal volume or the composition of the expired and inspired air. It can be used by a person skilled in the art to draw conclusions about the biological performance of the test subject. In the last line, the actual absolute performance is shown over time. It comprises the biological performance and the path and altitude profile from which the actual physical performance can be calculated. With the aid of such refined measured results the person skilled in the art can draw conclusions about the load capacity of the organism, and, for example, determine the training condition or the condition during a rehabilitation measure significantly more accurately.

What is claimed is:

1. A method for creating an individual movement profile for human and non-human animal test subjects, comprising the steps of:

continuously measuring absolute altitude;

recording movement of a test subject in three-dimensional space; and, creating a path and altitude profile of the test subject from results obtained in said continuously measuring step and said recording step.

2. The method for creating an individual movement profile for human and non-human animal test subjects according to claim 1, wherein said recording movement step includes recording acceleration of the test subject.

3. The method for creating an individual movement profile for human and non-human animal test subjects according to claim 1, further comprising the steps of:

measuring cardial and pulmonary variables of the test subject; and, recording the cardial and pulmonary variables of the test subject.

\* \* \* \* \*